United States Patent [19]

Chernack

[11] 4,402,420

[45] Sep. 6, 1983

[54] DUAL FUNCTION PORT CAP

[75] Inventor: Milton P. Chernack, West Hempstead, N.Y.

[73] Assignee: Extracorporeal Medical Specialties, Inc., King of Prussia, Pa.

[21] Appl. No.: 328,170

[22] Filed: Dec. 7, 1981

[51] Int. Cl.³ .............................................. B65D 41/34
[52] U.S. Cl. ........................................ 220/266; 150/8; 215/253
[58] Field of Search ............................. 150/8; 215/253; 222/541; 220/266, 276

[56] References Cited

U.S. PATENT DOCUMENTS 2,742,202 4/1956 Dresden et al. ...................... 222/541
4,248,227 2/1981 Thomas ........................... 222/541 X

FOREIGN PATENT DOCUMENTS 1432208 12/1968 Fed. Rep. of Germany ...... 215/253
1482521 1/1969 Fed. Rep. of Germany ...... 215/253
563189 3/1957 Italy ..................................... 215/253

Primary Examiner—Donald F. Norton
Attorney, Agent, or Firm—Lawrence D. Schuler

[57] ABSTRACT

A port cap for attachment to an inlet or an outlet port of a device, especially a medical device such as a cardiotomy reservoir, venous reservoir, blood oxygenator or blood dialyzer. The port cap comprises a hollow body member having a wall at its first end, a second end which is open, and a hollow interior. The closed end of the body member carries a hollow projection having a first end which is closed and a second end which is open, the hollow interior of this projection being in fluid communication with the hollow interior of the body member. The cap has a weakened peripheral portion near its closed end so that its closed end may be twisted off to gain access to the hollow interior of the cap. The cap may comprise thread means on the inside surface of the body member near its open end or it may have thread means on the outside surface of the aforementioned projection between the weakened peripheral portion and the end wall of the body member. The cap may be used to cover or close the port of a device. It can thereafter be completely removed from the port or, alternatively, the closed end portion thereof may be snapped off to provide a site at which auxiliary medical equipment can be connected.

10 Claims, 5 Drawing Figures

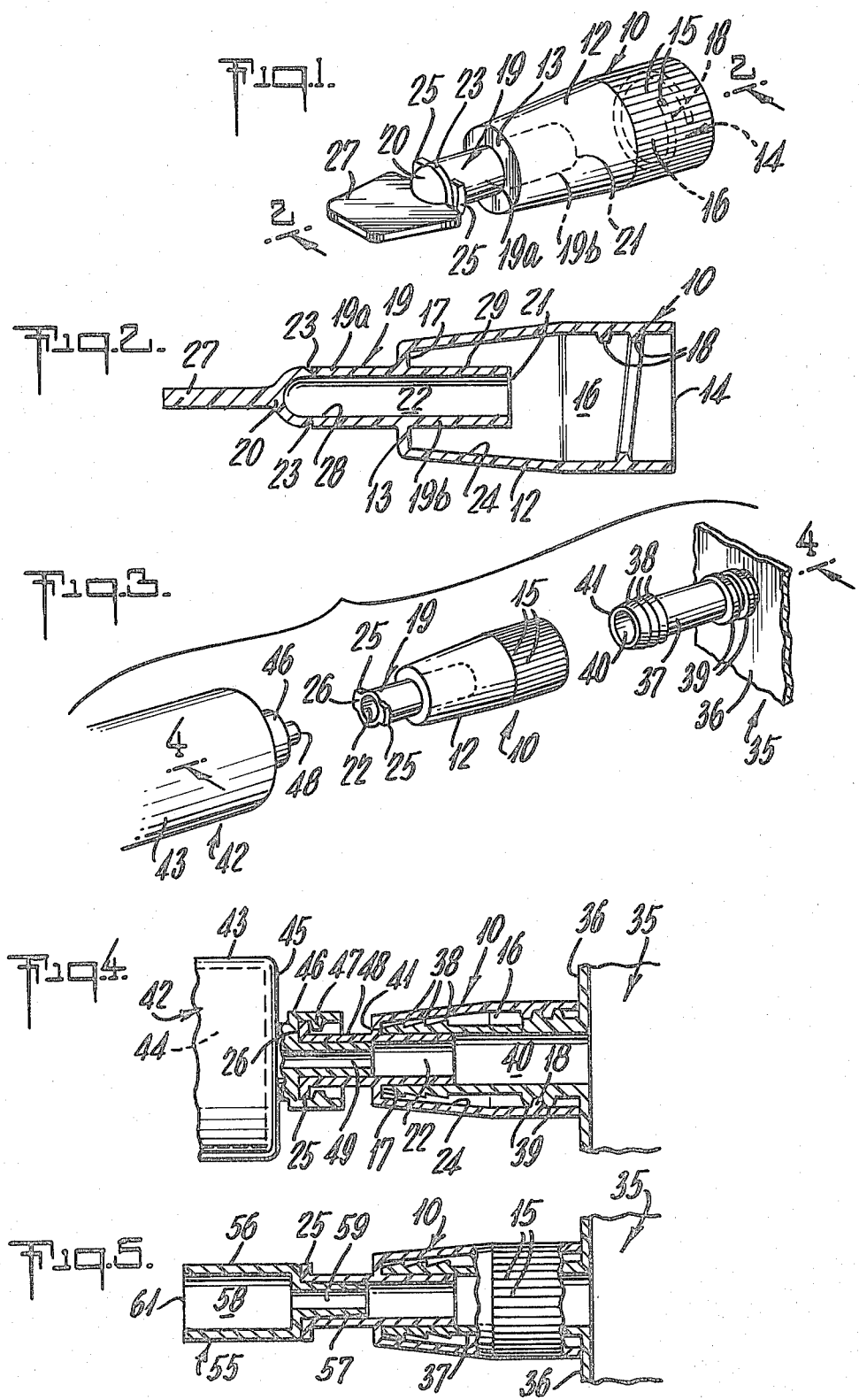

DUAL FUNCTION PORT CAP

FIELD OF THE INVENTION

The present invention relates to a cap for a port on a device in which fluids or solids may be contained or through which fluids may be circulated. In particular, the invention relates to a port cap having at one end thereof a portion which when broken away from the cap provides a site through which fluids may be injected into the device or at which additional equipment may be connected to the device. Even more particularly, the present invention relates to a threaded port cap having a portion which can be broken away to provide a standard luer fitting. If desired, the cap of the invention may be removed from the port to which it had been attached thus completely exposing that port for subsequent use. The cap is particularly useful with medical devices such as, for example, a cardiotomy reservoir or a venous reservoir used during cardio-pulmonary by-pass surgery.

BACKGROUND OF THE INVENTION

A variety of medical devices, for example, blood bags, blood oxygenators, blood dialyzers, venous reservoirs, and cardiotomy reservoirs, have inlet and ports through which fluids may be admitted to the interior of the device or through which fluids may be withdrawn from the device. Typically, these ports are relatively short lengths of hollow, more or less rigid plastic tubing which are sealed into one or more of the walls of the device. The protruding end of the port, which may include one or more tubing barbs, is used to receive conduit, e.g., flexible plastic tubing. Thus, for example a typical cardiotomy reservoir used as part of the extra-corporeal blood circuit during cardio-pulmonary by-pass surgery comprises two or more inlet ports and at least one outlet port. A suction line or lines from the operative site may be attached to one or more of the inlet ports. In addition, pieces of tubing from sources of banked blood and other medical fluids are connected to other inlet ports. Another piece of tubing connects the blood outlet port of the cardiotomy reservoir to the inlet of a cardiotomy blood filter.

Medical devices of the kind mentioned above are sterilized by the manufacturer prior to delivery to the end-user. Prior to the sterilization operation the inlet ports and the outlet ports of the device are covered with port caps. Where, for example, the port on the device consists of a short piece of relatively rigid hollow plastic tubing, there is frictional engagement between the inner surface of the port cap and the outer surface of the plastic tubing. If the port on the device has the aforementioned tubing barbs, there is frictional engagement between the inner surface of the port cap and the outer surfaces of the outer edges of the tubing barbs. The aforementioned frictional engagement keeps the port cap in place and prevents entry of contaminating matter through the port into the interior of the device. In order to preserve the sterility of the inner surfaces of the device, the port caps are left in place over the various ports while the device is being unpacked and set up for use. The caps are removed when it is desired to expose the port so that suction tubing or fluid flow tubing, etc. may be connected thereto. The port cap, once it is removed, is not ordinarily used to again cover the port.

In some instances it may be necessary to add a measured amount of a medication to a medical device at the time it is to be used. For example, in the case of a cardiotomy reservoir it may be necessary to add an anticoagulant prior to actual start-up of the surgical procedure. Such medication is usually added in relatively small amounts which must be measured accurately. A syringe is often used to accurately measure and dispense the desired medication. An ordinary inlet or outlet port is not suitable for this purpose because it is designed only to receive tubing and is not adapted to receive auxiliary medical equipment, such as a syringe, in a secure leak-proof manner.

Thus it would be quite advantageous to provide a port cap which could be removed in the usual way from a port of a device to expose said port for connection to suction tubing or fluid flow tubing or which, alternatively, could be used for the secure connection of auxiliary equipment to said port. Such a port cap would increase the versatility of the device and allow auxiliary equipment to remain securely connected to the medical device until it was time to use the same. The personnel using the device would have the option of using the port as an injection site as well as using it for the purpose of making flexible connections.

SUMMARY OF THE INVENTION

In its broadest form, the port cap of the present invention comprises a hollow body member having a first end, a second end which is open, and a tubular element extending from said first end. The tubular element which is also hollow, has a first end which is closed and a second end which is open. The hollow interior of the tubular element communicates with the hollow interior of the body member of which it is a part. The tubular element includes a weakened peripheral portion intermediate its closed end and the first end of the aforementioned body member, thus allowing the closed end portion of the tubular element to be easily broken away to permit ready access to its hollow interior.

The port cap of the invention can be placed over a port of a medical device, the interior surface of the body member being sized so as to provide a friction fit with some portion of the outer surface of said port. The cap is put in place prior to the sterilization procedure and is thereafter kept in place to preserve sterility during transit and prior to use. At the time of use, the port cap may be completely removed so that, for example, flexible tubing may be connected to the thus exposed port. If it is desired, e.g., to add a medication or a fluid, such as blood or isotonic saline, to the device, the cap itself may be left in place and the closed end of the tubular element may be snapped off, thus exposing the hollow interior of the port cap. Medication or other fluid may then be injected through the communicating hollow interior of the tubular element and the body member, then through the lumen of the port to which the port cap is attached and finally into the interior of the device itself.

In another embodiment of the port cap of the present invention, the body member comprises interiorly located threads near its open end. These threads allow the cap to be placed over an inlet or outlet port of a device and held there securely, the interiorly located threads of the port cap being engaged with mating exteriorly located threads at the base of the port where it joins the wall of the medical device.

In a different embodiment of the port cap of the invention, at least a portion of the interior surface of the aforementioned tubular projection between its weakened peripheral portion and the first end of the body member is tapered. When the closed end of the tubular element is broken away at the weakened peripheral portion, there is exposed a tapered female portion to which can be inserted a correspondingly tapered male fitting.

In still another embodiment of the invention, the exterior surface of the tubular projection comprises thread means which are located intermediate the first end of the body member and the weakened peripheral portion. Preferably, these threads are standard Luer threads and are located just adjacent the weakened peripheral portions. When the closed end portion of the tubular element is snapped off there is provided a male Luer fitting to which may be connected an item of auxiliary equipment having a female Luer fitting.

In yet another embodiment of the invention, the aforementioned tubular element extends into the interior of the body member and has an externally tapered surface. A cap having this construction can be friction fitted to a port having a correspondingly tapered internal surface.

The port cap of the present invention may include a body member which is internally threaded adjacent its open end and the aforementioned, exteriorly tapered element extending into the interior of the body member. Such a port cap can be used to cover in fluid tight relationship an inlet or outlet port which is internally tapered and which carries mating threads on the periphery of its base. When a port cap of this construction is placed over such a port, and connected with a turning motion, the mating of the interiorly located threads of the body member with the threads on the exterior of the port provide a positive connection of the two parts. At the same time, the tapered exterior of the internally located portion of the tubular projection is put into sealing contact with the correspondingly tapered internal surface of the port. This is extremely advantageous because the port cap is positively locked in place over the port, thus preventing accidental disengagement thereof.

In addition, as a result of the mating of the aforementioned tapered surfaces, there is provided, when the closed end of the tubular element is snapped off, a path for the flow of fluid through the port, this path comprising the lumen of the port itself and the hollow interior of the tubular element comprising the port cap.

In accordance with one preferred aspect of the present invention, there is provided a port cap comprising a body member having a wall at its first end, a second open end, and a hollow interior, the inner surface of said hollow member comprising thread means located near said open end, a tubular element extending through the wall at the first end of said body member into the hollow interior of said body member, said tubular element having a first end which is closed, a second end which is open, and a hollow interior, a first portion of said tubular element including its closed end being located exteriorly of said body member and a second portion of said tubular element including its open end being located within the hollow interior of said body member, the hollow interior of said tubular element being in fluid communication with the hollow interior of said body member, said first portion of said tubular element having a weakened peripheral portion intermediate its closed end and the first end of said body member, the outer surface of said first portion including thread means located between said weakened peripheral portion and the first end of said body member. In accordance with another preferred aspect of the present invention, the exterior surface of that portion of the tubular element which extends into the interior of the body member is tapered. In either of the foregoing cases, it is preferred, but not necessary, that the interior surface of that portion of the tubular element which is located exteriorly of the body member be tapered.

In all of the embodiments mentioned, it is preferred, although not necessary, that the port cap be sized so that when it is in place over the port, the outer annular surface of the port comes into sealing contact with the inner surface of the end wall of the body member.

BRIEF DESCRIPTION OF THE DRAWINGS

The present invention will be more readily understood with reference to the appended drawings in which:

FIG. 1 is a perspective of one embodiment of the port cap of the present invention;

FIG. 2 is a sectional view taken along line 2—2 of FIG. 1;

FIG. 3 is perspective showing the port cap of the present invention after removal of its closed end portion and illustrating use thereof in conjunction with a medical device (shown in fragment) and a dispensing syringe (also shown in fragment);

FIG. 4 is a view partly in fragment and partly in cross-section showing in detail the assembly of the components in FIG. 4; and FIG. 5 is a view similar to FIG. 4 and illustrating in cross-section the use of the port cap of the present invention to connect a modified dispensing syringe to the inlet port of a medical device.

DETAILED DESCRIPTION OF THE INVENTION

Referring now to the drawings, and especially to FIGS. 1 and 2 thereof, there is shown one embodiment of a port cap in accordance with the present invention. Port cap 10 comprises a body member 12 having a wall at its first end 13 and a second end 14 which is open. The body member is generally cylindrical in shape near its open end, and the peripheral wall thereof slopes slightly inwardly toward its closed end. As best seen in FIG. 3, body member 12 comprises a plurality of shallow, narrow grooves 15 near its open end. These grooves, which preferably run longitudinally of the port cap, facilitate grasping of the cap during positioning over, or removal from, an inlet or outlet port. Body member 12 has a hollow interior 16 and includes interiorly located threads 18 near its open end 14.

Port cap 10 further comprises a projection 19 associated with the closed end of the body member. Projection 19 has a first end 20 which is closed, a second end 21 which is open, and a hollow interior 22. This hollow interior 22 is in fluid communication with hollow interior 16 of the body member. In the embodiment under discussion, projection 19 is generally cylindrical in shape and its closed end 20 is rounded off as can be seen in FIG. 2. Projection 19 preferably has a diameter which is smaller than the diameter of body member 12 measured at its closed end 13.

Projection 19 has a weakened peripheral portion which can be formed, for example, by cutting away some of the material comprising the wall of the projection to leave a thinned portion 23. This weakened peripheral portion is located intermediate the wall at first end 13 of body member 12 and the closed end 20 of projection 19. Preferably, the weakened portion is located a short distance from closed end 19 of the projection.

Projection 19 further comprises thread means 25 which are located on its outer surface intermediate the wall at first end 13 of body member 12 and the aforementioned weakened peripheral portion 23. Preferably, threads 25 are standard luer threads and they are located just adjacent the weakened peripheral portion of projection 19.

It is preferred that closed end 20 of projection 19 carry a grasping means which, in the embodiment under discussion, take the form of a flattened tab 27.

In accordance with a preferred aspect of the invention, projection 19 comprises a first part 19a and a second part 19b, the former part being located exteriorly of body member 12 and the latter part extending into hollow interior 16 of body member 12. Preferably, the interior surface 28 of projection 19 is constructed with a standard taper and the exterior surface 29 of part 19b is constructed with a tapered surface.

In its broadest aspect, the port cap of the present invention comprises body member 12 and projection 19 with its weakened peripheral portion, these parts being constructed and arranged as described above. Threads 18 on the body member need not be present if the interior dimensions of the body member near its open end are sized so as to provide a snap fit or a friction fit over the port which is to be covered. Neither is it necessary in the broadest embodiment that projection 19 extend into the hollow interior of the body member or that said projection carry threads 25 or that part 19a be internally tapered or that part 19b be externally tapered. The port cap in its broadest aspect can be used to cover or close any inlet or outlet port. If it is desired to expose the port, for example in order to attach a length of flexible tubing thereto, the port cap is simply grasped and removed from the port. If it is desired to add a liquid to the interior of the device of which the port is a part, it is possible to manipulate, with, for example, a turning or twisting motion, the closed end of projection 19 so that it breaks away at its weakened peripheral portion. It is then possible to add the desired liquid, e.g., with a syringe having a needle, through the hollow interior of the remaining part of the port cap into the device.

In one narrower aspect of the invention, the body member of the port cap can include interiorly located threads 18 which can be engaged with corresponding threads on an inlet or outlet port of a device (such as a medical device 35 illustrated infragment in FIG. 3) to insure the cap is firmly in place and will not be accidentally dislodged.

In another narrower aspect of the invention, a taper is imparted to at least a portion of interior surface 28 of part 19a of projection 19 between the weakened peripheral portion and the wall at first end 13 of body member 12. This tapering begins at the weakened peripheral portion and extends toward the wall at end 13 of the device. As a result of this tapering, the inside diameter of part 19a is relatively larger near the weakened peripheral portion and becomes gradually smaller as it approaches the wall at first end 13 of body member 12. When the closed end portion of projection 19 is then broken away, the port cap has a tapered female fitting which can receive a correspondingly tapered male fitting associated with an auxiliary item of medical equipment such as, e.g., a syringe or a length of conduit.

In still another narrower aspect of the invention, the outer surface of part 19a of projection 19 carries threads 25 (which are preferably luer threads) intermediate the wall at first end 13 of body member 12 and the weakened peripheral portion of projection 19. When the closed end of projection 19 is broken away at the weakened peripheral portion, projection 19 with its externally located threads 25 comprise a male fitting which can engage a correspondingly threaded female fitting associated with an aforementioned item of auxiliary medical equipment.

It will be recognized that the port cap of the invention may include both of the features set forth in the two preceding paragraphs, that is, the interior surface of part 19a may be tapered and the exterior surface of part 19a may carry threads 25. The advantage of this construction is apparent. When the closed end portion of projection 19 is broken away the port cap includes a fitting which is internally tapered and has externally located threads. This fitting is available to engage another fitting which comprises internally located matching threads and a projecting portion which is externally tapered. When the two fittings are assembled and turned to engage their threads, the mating tapered surfaces of the two fittings provide a fluid tight seal and the engaged threads of the two fittings preclude accidental dislodgement.

In yet another narrower aspect of the invention, the port cap may be constructed so that a part 19b of projection 19 extends into the hollow interior of body member 12 and at least a portion of the outer surface of said extending part 19b is provided with a standard taper. In this case, the tapering begins at open end 21 of projection 19 and extends (in the leftward direction in FIG. 2) toward the inner surface 17 of the wall at end 13 of body member 12. As a result of this tapering, the outside diameter of part 19b is relatively smaller at open end 21 and becomes gradually larger as it approaches inner surface 17. A port cap having this construction can be used to close an inlet or outlet port on a medical device if said inlet or outlet port includes an interior portion which is correspondingly tapered, said two tapered surfaces, when they are properly engaged, forming a fluid tight seal. The use of interiorly located threads 18 near the open end of body member 12 for engagement with corresponding threads on the inlet or outlet port will provide against accidental dislodgement of the engaged fittings.

The most preferred embodiment of the port cap has been described earlier herein with reference to FIGS. 1 and 2, said most preferred embodiment including threads 18 at the interior of the open end of the body member, the extension of part 19b of projection 19 into the hollow interior of the body member, the external tapering of part 19b, the internal tapering of part 19a of projection 19, the provision of thread means 25 on the external surface of projection 19, and the provision of grasping means at the closed end of projection 19.

The various ways of using the most preferred embodiment of the invention, and the advantages to be derived therefrom, will now be described with reference to FIGS. 3-5 of the drawings. As mentioned, the port cap of the present invention is intended primarily for use with medical devices such as a venous reservoir, cardiotomy reservoir, blood oxygenator, blood dialyzer and the like, but it will be appreciated that it may be advantageously used with a variety of other devices having inlet and outlet ports.

For the sake of convenience, use of the port cap of the invention will be described herein in connection with its use with a medical device.

The first use to which port cap 10 may be put is to cover the inlet and outlet ports on a medical device after assembly of the same. The port cap is put in place prior to packaging and sterilization; it thereafter remains in place until the device is to be used in a medical or surgical procedure.

FIG. 3 shows in fragmentary view a medical device such as a cardiotomy reservoir 35 comprising a wall 36 in which there is a port 37. Port 37 is a small piece of rigid plastic having a continuous lumen 40 therethrough, which lumen is in fluid communication with the interior of the cardiotomy reservoir. Port 37 has the usual "tubing barbs" 38 and has threads 39 at its base, i.e., at the point where the port is sealed into wall 36. FIG. 3 also shows in perspective port cap 10, the closed end of which has been broken away at its weakened peripheral portion, thus providing access to the externally located luer threads 25 and the hollow interior 22 of projection 19. Shown in fragmentary view at the left hand side of FIG. 3 is a syringe 42, this syringe being illustrative of any of a number of auxiliary medical devices which it may be desired to connect to port 37 of a medical device such as cardiotomy reservoir 35 by use of port cap 10. Syringe 42 comprises a barrel 43 having a hollow interior 44 and the usual plunger (not illustrated in the drawings). The front wall 45 of the syringe has a reduced diameter portion 46 having internally disposed luer threads 47. Emerging centrally of reduced diameter portion 46 is a short nozzle 48 having a continuous lumen 49 communicating with the hollow interior 44 of the syringe, thus allowing a fluid to be drawn into or ejected from the syringe barrel by means of a plunger (not shown in the drawings). There is a clearance between the apices of threads 47 and the outer surface of nozzle 48.

FIG. 4 is a cross-sectional view of the three components of FIG. 3 in their fully assembled configuration. Port cap 10 (with its break-away portion removed) has been screwed onto port 37 so that threads 18 on the inner surface of the body member of the port cap are in engagement with exterior threads 39 on port 37. The port cap is appropriately sized so that annular facing surface 41 (best seen in FIG. 3) at the outer tip of port 37 has been brought into contact with the interior surface 17 of end wall 13 of body member 12 to thereby provide a leak-proof seal. It will be noted that inwarding extending part 19b of the port cap is disposed within lumen 40 of port 37. This disposition of part 19b within lumen 40 provides additional sealing if the outer surface of 19b and the inner surface of port 37 are correspondingly tapered. It will be noticed that body member 12 has been sized so that when port cap 10 is in place over port 37, there is a slight clearance between the inner wall surface 24 of the body member and tubing barbs 38. In the assembled configuration, hollow interior 22 of projection 19 is in fluid communication with the interior of cardiotomy reservoir 35 through lumen 40 of port 37.

FIG. 4 also shows, at its left hand side, how syringe 42 is connected to part 19a of projection 19 of the port cap in the assembled configuration. Internal threads 47 on the reduced diameter portion 45 of the syringe are in engagement with threads 25 on the outer surface of part 19a of projection 19 of port cap 10. The facing surface 26 (see FIG. 3) of port cap 10 (its closed end having been snapped off) is in contact with the inner end wall of reduced diameter portion 46 of the syringe to form a fluid-tight seal. Nozzle 48 is disposed in the hollow interior 22 of projection 19. This arrangement allows for additional sealing in the instance where the nozzle 48 is exteriorly tapered and part 19a of projection 19 is correspondingly interiorly tapered. When the various parts are assembled as illustrated in FIG. 4 there is continuous, leak-proof fluid communication from interior 44 of syringe 42, through lumen 49 of nozzle 48, the interior 22 of projection 19, the lumen 40 of port 37, into the interior of cardiotomy reservoir 35.

FIG. 5 shows a modification of FIG. 4 in which port cap 10 is screwed onto port 37 in the same fashion as shown in FIG. 4. At the left hand side of FIG. 5 there is shown a connector 55 comprising a hollow tubular element 56 which has a reduced diameter portion 57 at one of its ends. Lumen 58 of tubular element 56 is in fluid communication with lumen 59 of reduced diameter portion 57. Tubing (not illustrated) may be attached in known fashion to end 61 of the connector for delivery of a fluid therethrough to the interior of device 35. The interior surface of part 19a of projection 19 is preferably tapered in the manner mentioned earlier so as to provide a seal with the correspondingly tapered outer surface of reduced diameter portion 57.

The port cap of the invention can be readily injection molded from a variety of injection molding grade resins. Low density polyethylene is a preferred material of construction but other materials such as nylon, polycarbonate, or acrylonitrile-butadiene-styrene (ABS) resin can be used, if desired. The caps can be provided in different colors by adding a suitable pigment to the molding resin. The particular color of a cap may be employed to indicate the nature or function of the port to which it is attached. For example, a white or clear (non-pigmented) cap attached to an inlet port on a cardiotomy reservoir might indicate that fluids (e.g., blood) entering through that port would next be conducted to a filtering section; a blue cap attached to other ports on a cardiotomy reservoir might indicate those ports are intended to function as inlet ports for suction lines or left ventricular sump lines; a red cap attached to a port might indicate that such port is intended to accept medication, e.g., heparin, which does not require filtering; and a yellow cap attached to a port might indicate that such port is intended to serve as a vent means or as a site to which a vacuum source can be attached.

I claim:
1. A port cap comprising:
   a. a body member having a wall at its first end, a second end which is open, and a hollow interior,
   b. a projection on the wall at the first end of said body member, said projection having a first end which is closed, a second end which is open, and a hollow interior, the hollow interior of said projection being in fluid communication with the hollow interior of said body member,
   c. said projection having a weakened peripheral portion located intermediate the wall at the first end of said body member and the closed end of said projection, at least a portion of the interior surface of said projection between said weakened peripheral portion and the wall at the first end of said body member being tapered.
2. A port cap according to claim 1 wherein the body member has interiorly located thread means near its open end.

3. A port cap comprising:
a. a body member having a wall at its first end, a second end which is open, and a hollow interior,
b. a projection on the wall at the first end of said body member, said projection having a first end which is closed, a second end which is open, and a hollow interior, the hollow interior of said projection being in fluid communication with the hollow interior of said body member,
c. said projection having a weakened peripheral portion located intermediate the wall at the first end of said body member and the closed end of said projection, the exterior surface of said projection comprising thread means which are located intermediate the wall at the first end of said body member and said weakened peripheral portion.

4. A port cap according to claim 3 wherein said projection extends into the interior of said body member.

5. A port cap according to claim 3 wherein the outer surface of that part of the projection which extends into the hollow interior of said body member is tapered.

6. A port cap according to claim 3 wherein the body member has interiorly located thread means near its open end.

7. A port cap comprising a body member having a wall at its first end, a second end which is open, and a hollow interior, the inner surface of said hollow member comprising thread means located near said open end, a tubular element extending through the wall at the first end of said body member into the hollow interior of said body member, said tubular element having a first end which is closed, a second end which is open, and a hollow interior, a first portion of said tubular element including its closed end being located exteriorly of said body member and a second portion of said tubular element including its open end being located within the hollow interior of said body member, the hollow interior of said tubular element being in fluid communication with the hollow interior of said body member, said first portion of said tubular element having a weakened peripheral portion intermediate its closed end and the wall at the first end of said body member, the outer surface of said first portion including thread means located between said weakened peripheral portion and the wall at the first end of said body member.

8. A port cap according to claim 7 in which at least part of the interior surface of said first portion between said weakened peripheral portion and the wall at the first end of said body member is tapered.

9. A port cap according to claim 7 in which at least part of the exterior surface of said second portion between the open end of said projection and the wall at the first end of said body member is tapered.

10. A port cap according to claim 7 in which at least part of the interior surface of said first portion between said weakened peripheral portion and the wall at the first end of said body member is tapered and in which at least part of the exterior surface of said second portion between the open end of said projection and the wall at the first end of said body member is tapered.

* * * * *